(12) United States Patent
Kempers et al.

(10) Patent No.: US 9,416,337 B2
(45) Date of Patent: Aug. 16, 2016

(54) ESTER SYNTHESIS

(71) Applicant: BASF SE, Ludwigshafen (DE)

(72) Inventors: Peter Kempers, Mönchengladbach (DE); Ulrich Schörken, Düsseldorf (DE); Rolf Kawa, Monheim (DE); Jörg Schwarzer, Hilden (DE); Thomas Wolf, Haan (DE)

(73) Assignee: BASF SE, Ludwigshafen (DE)

( * ) Notice: Subject to any disclaimer, the term of this patent is extended or adjusted under 35 U.S.C. 154(b) by 77 days.

(21) Appl. No.: 14/047,212

(22) Filed: Oct. 7, 2013

(65) Prior Publication Data

US 2014/0170717 A1 Jun. 19, 2014

Related U.S. Application Data

(60) Provisional application No. 61/711,761, filed on Oct. 10, 2012.

(51) Int. Cl.
*C12P 7/62* (2006.01)
*C11C 3/00* (2006.01)
*C12P 7/64* (2006.01)

(52) U.S. Cl.
CPC ............... *C11C 3/003* (2013.01); *C12P 7/6436* (2013.01)

(58) Field of Classification Search
None
See application file for complete search history.

(56) References Cited

U.S. PATENT DOCUMENTS

| 4,826,767 | A | 5/1989 | Hansen |
| 7,811,802 | B2 * | 10/2010 | Hirose et al. ................... 435/198 |
| 2010/0159538 | A1 | 6/2010 | Both et al. |

FOREIGN PATENT DOCUMENTS

| EP | 0383405 B1 * | 6/1993 |
| WO | WO-2007/017167 | 2/2007 |

OTHER PUBLICATIONS

Wehtje, E., D. Costes, and P. Adlercreutz. "Continuous lipase-catalyzed production of wax ester using silicone tubing." Journal of the American Oil Chemists' Society 76.12 (1999): 1489-1493.*
Wehtje, Ernst, et al. "Water activity control in enzymatic esterification processes." Enzyme and microbial technology 21.7 (1997): 502-510.*
PCT International Search Report, dated Nov. 7, 2013, 3 pgs.
PCT Written Opinion in PCT/EP2013/070408, dated Nov. 7, 2013, 10 pgs.
Hill, G , "Industrial Use of Lipases to Produce Fatty Acid Esters", *European Journal of Lipid Science and Technology*, vol. 105, No. 10 Sep. 29, 2003, 602-604.

* cited by examiner

*Primary Examiner* — Robert Yamasaki
(74) *Attorney, Agent, or Firm* — Marshall, Gerstein & Borun LLP

(57) ABSTRACT

The present invention relates to a process for preparing esters from fatty alcohols, in which fatty alcohols and fatty acids are reacted in the presence of an enzyme at a temperature in the range of 30 to 50° C., the water which forms is removed and the reaction is completed under reduced pressure at a temperature of 50 to 80° C.

17 Claims, 1 Drawing Sheet

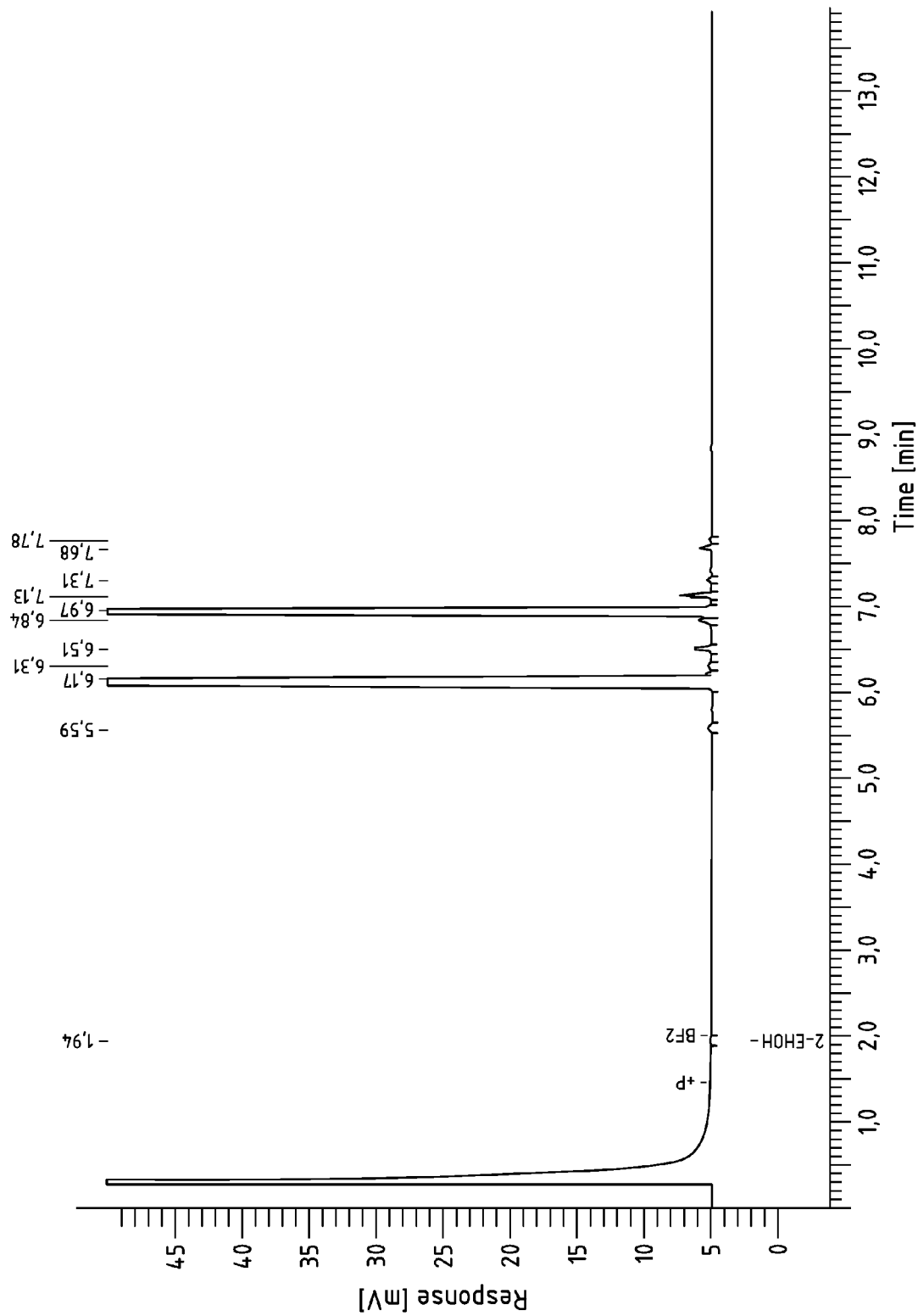

ESTER SYNTHESIS

CROSS REFERENCES TO RELATED APPLICATIONS

This application claims priority to U.S. Provisional Application 61/711,761, filed Oct. 10, 2012, the contents of which are incorporated by reference.

FIELD

The present invention comprises a process for preparing esters from fatty alcohols and fatty acids in which the predominant part of the water formed during the synthesis is removed in liquid form.

BACKGROUND

The enzymatic synthesis of esters from fatty alcohols and fatty acids is known. Enzymatic synthesis is an environmentally friendly process, in which the synthesis takes place with complete evaporation of the water of reaction formed.

The industrial use of lipases for preparing fatty acid esters has been described, for example, by Geoffrey Hills in Eur. J. Lipid Sci. Technol. 105, 2003, pp. 601-607. The fatty acid esters produced, particularly myristyl myristate, are produced in a fixed-bed process, in which the reactants are pumped several times through the column and the water of reaction formed is evaporated off under reduced pressure.

Fatty acid esters are used to an increasing degree in cosmetic skin care products as oil bodies or emollients. In order to meet the high demands of the market with respect to sensory properties and optimal dermatological tolerance, novel oil bodies and oil body mixtures are continuously being developed and tested. Innovative technologies for preparing these fatty acid esters are also part of this.

The synthesis of esters from fatty alcohols and fatty acids, as previously stated, forms water which must be removed in order to shift the reaction equilibrium towards a complete synthesis. The enzymatically catalysed preparation of fatty acid esters must be performed at relatively low temperatures, in order to maintain the optimal enzyme stability. Accordingly, a very strong vacuum is required to evaporate the water. This evaporation is very energy-intensive.

It has additionally been shown that problems arise when scaling-up to batch reactors. In typical production reactors of 10-100 $m^3$, the water evaporation occurs, by means of the pressure drop, only in the upper layers due to the fill depth. It has further been found that the reaction is very rapid up to a conversion of 80-90% and typically proceeds in less than five hours. However, the result of this is that the amount of water formed in a production reactor during this period cannot be removed by industrial means, or can be removed only with very large equipment resources. Furthermore, the required energy input, which is necessary for the evaporation of the water of reaction, can be introduced into the reactor only with difficulty owing to the low internal temperature in the reactor.

A further problem lies in the fact that the enzyme catalyst has only very low stability at high temperatures or becomes inactive. It is known that enzymes are very temperature-sensitive. Thus, the ester synthesis cannot take place at temperatures greater than 60-80° C. It has particularly been found that the long-term stability of the enzymes falls in the presence of short-chain alcohols and short-chain fatty acids (C8/C10) at even lower temperatures, from about 40° C., such that the reaction should ideally be carried out at temperatures around 40° C.

SUMMARY

Based on these problems and disadvantages of the enzymatic ester syntheses of the prior art, an object of the present invention is to establish a technology with which it is possible to prepare esters from fatty alcohols and fatty acids, where a lower overall energy consumption is ensured, no problems on scaling-up to large batch reactors occur and an improved enzyme stability is ensured.

This object has been achieved with the process according to patent claim 1.

The present invention relates to a process for preparing esters from fatty alcohols and fatty acids comprising the steps:

reaction of fatty alcohols of the formula $R^1$—OH, where $R^1$ is an aliphatic linear or branched hydrocarbon group having 6 to 22 carbon atoms, and fatty acids of the formula $R^2$—COOH, where $R^2$ is an aliphatic linear or branched hydrocarbon group having 6 to 22 carbon atoms, in the presence of enzyme at a temperature in the range of 30 to 50° C., until the reaction equilibrium is achieved;

removal of the water formed during the reaction and completion of the reaction under reduced pressure at a temperature of 50 to 80° C.

The dependent claims define preferred embodiments of the process according to the invention.

The process according to the invention for preparing esters from fatty alcohols and fatty acids is an effective solution for the problems and disadvantages which have become clear from the corresponding processes according to the prior art. The present process is a three-stage enzymatic procedure, in which synthesis is performed initially without reduced pressure at a low temperature until the reaction equilibrates. In a second step the water of reaction is removed. In the next, third reaction step, the fatty acid ester is synthesized, at a higher temperature than in step 1, under reduced pressure, until full conversion.

BRIEF DESCRIPTION OF THE DRAWINGS

FIG. 1 shows the GC chromatogram of an ester prepared according to the invention after purification by distillation.

DETAILED DESCRIPTION

In a preferred embodiment of the process according to the invention, synthesis is performed during the completion of the reaction, i.e. until full conversion, in a stripping gas atmosphere. All conventional stripping gases can be used as stripping gas.

Examples of suitable stripping gases are nitrogen, air, carbon dioxide and argon, although nitrogen is preferably used as stripping gas.

An essential characteristic of the process according to the invention is that the first step is operated initially without reduced pressure, until the reaction equilibrium is achieved. Not until after the removal of the water formed during the reaction, by decanting for example, is the reaction started again according to the invention, then with application of reduced pressure. During this completion of the reaction, a pressure of 100 to 10 000 Pa is employed. In a preferred embodiment of the process according to the invention a pressure of 1500 to 4500 Pa is employed during the completion.

The reaction, which is carried out at the beginning without reduced pressure, is carried out at relatively low temperatures. A temperature range of 35 to 45° C. is preferably selected.

During the completion of the reaction, a higher temperature range of 55 to 65° C. is ideally employed.

The process according to the invention can be carried out in the presence of any enzyme, provided that this enzyme is capable of catalyzing synthesis of esters from fatty alcohols and fatty acids. In practice it has proven advantageous that a lipase is used as enzyme. A preferred lipase is lipase B, ex *Candida antarctica*, for example. The enzyme is preferably used in immobilized form. A preferred method for immobilizing is, for example, adsorption onto a support material. Examples of support materials are Accurel MP 1000 and Lewatit VPOC 1600. In practice, it has proven advantageous to use the immobilized enzyme in the synthesis in an amount of 0.5 to 5.0% by weight. A particular advantage of the enzyme catalyst immobilized on a support is also that this can readily be retained by way of a mesh or filter during the water formed during the reaction.

The process according to the invention can be carried out, for example, as follows:

In the first step of the enzymatic synthesis, the mixture in the batch reactor is mechanically agitated, e.g. stirred, until reaction equilibrium has been achieved. In this step, at least 80% ester product conversion is achieved.

In the intermediate step of the removal of the water formed during the reaction, the mechanical agitation of the batch is stopped, whereupon the water is allowed to separate out, preferably for 0.5 to 2 hours. The water is ideally drawn off via a bottom outlet, while the immobilized enzyme is retained, for example by means of a mesh in the reactor or filter unit.

The last step of the completion of the reaction under reduced pressure is carried out in the same batch reactor up to a conversion of at least 95%, preferably greater than 95%, ester product conversion. Ideally, the enzyme from the first step can be used again, so that, from an economic point of view, the immobilized enzyme can be reused for the overall synthesis.

The fatty alcohols and fatty acids used as starting materials in the ester synthesis may be industrial fatty alcohols or fatty acids. Preferably, however, the fatty alcohols and fatty acids are obtained from renewable raw materials.

Fatty alcohols are understood to mean primary aliphatic alcohols of the formula

$R^1$—OH where $R^1$ is an aliphatic, linear or branched hydrocarbon residue having 6 to 22 carbon atoms. Also included are unsaturated hydrocarbon residues having at least one double bond. Typical examples are caproyl alcohol, capryl alcohol, 2-ethylhexyl alcohol, capric alcohol, lauryl alcohol, isotridecyl alcohol, myristyl alcohol, cetyl alcohol, palmoleyl alcohol, stearyl alcohol, isostearyl alcohol, oleyl alcohol, elaidyl alcohol, petroselinyl alcohol, linolyl alcohol, linolenyl alcohol, elaeostearyl alcohol, arachyl alcohol, gadoleyl alcohol, behenyl alcohol, erucyl alcohol and brassidyl alcohol and also mixtures thereof. Preference is given to fatty alcohols having 8 to 18 carbon atoms.

Fatty acids are understood to mean aliphatic carboxylic acids of the formula

$R^2COOH$ where $R^2$ is an aliphatic, linear or branched hydrocarbon residue having 6 to 22 carbon atoms. Also included are unsaturated hydrocarbon residues having at least one double bond. Typical examples are caproic acid, caprylic acid, 2-ethylhexanoic acid, capric acid, lauric acid, isotridecanoic acid, myristic acid, palmitic acid, palmitoleic acid, stearic acid, isostearic acid, oleic acid, elaidic acid, petroselinic acid, linoleic acid, linolenic acid, elaeostearic acid, arachidic acid, gadoleic acid, behenic acid and erucic acid and also mixtures thereof. Preference is given to industrial fatty acids having 8 to 18 carbon atoms.

The process according to the invention for preparing the ester is preferably conducted in a one-pot process. A preferred reactor for this purpose is the batch reactor or a batch reactor having fixed-bed loops.

For processing the fatty acid esters prepared according to the invention, further purification and preservation steps may be carried out. These include for example a forerun distillation for removal of unreacted reactants. For instance, a product distillation for improving color can also be carried out. It has been found that a deodorization for optimizing odor can also be successfully carried out. For instance, the addition of antioxidants (such as tocopherol) may also be desirable for stabilizing the product.

The process according to the invention has very many advantages compared to the known processes for preparing fatty acid esters. One significant improvement is that an extremely low amount of energy is consumed overall since less water is evaporated compared to the processes in the prior art, in which the entire reaction is carried out under reduced pressure.

In the intermediate stage of the second step, i. e. the removal of the water, the latter can be separated off advantageously using a bottom outlet, since the water separates very rapidly from the hydrophobic esters. In large batch reactors, this allows shorter reaction times to be achieved than complete evaporation of the water of reaction. The conversion to the reaction equilibrium state is practically independent of batch size, and is influenced mainly by the mixing.

A further advantage is that an exceptional improvement in enzyme stability is achieved. The reason is that the first process step is carried out at a considerably lower temperature than the third step. Furthermore, in the third step the concentration of deactivating components, such as starting materials, is distinctly lower.

Finally, a very good final conversion is observed. This is attributed to the higher temperature employed in the third step. Consequently, a conversion of up to more than 99% product is possible. The additional use of a stripping gas further promotes an increase in the final conversion.

The following examples serve to illustrate the process according to the invention.

EXAMPLES

Example 1

Long-Term Stability of the Enzyme in the 3-Step Process (Laboratory Scale)

Lewatit VPOC 1600 (Lanxess) and commerically available lipase B ex *Candida antarctica* (Lipozyme CalB L from Novozymes) in a 1:1 ratio were stirred overnight at room temperature in 20 times the amount of water. The immobilized enzyme was filtered off and used directly for the synthesis.

In a 1 L reactor with paddle stirrer, 650 g of an equimolar mixture of octanol and fatty acid (industrial mixture of octanoic acid and decanoic acid) were reacted with 2% by weight of immobilized enzyme. The mixture was stirred at 45° C. for 4 h at atmospheric pressure. Stirring was stopped after 4 h and a sample was removed for determination of the acid number. After 30 min the water phase was drained off from the reactor and the reaction was restarted. The temperature was raised to 60° C., an oil pump vacuum of 20 mbar was applied and the reaction mixture was flushed with nitrogen. The batch was stirred for a further 18 h under constant conditions. Following this reaction period, the batch was drained off, the conversion was determined by measuring the acid number and a new batch was initiated under the same conditions with the same enzyme. In total, 10 batches were processed with the same enzyme. The starting acid number of the fatty alcohol/fatty acid mixture was 210.

| Batch | Acid no. 4 h | Conversion 4 h | Acid no. 22 h | Conversion 22 h |
|---|---|---|---|---|
| 1 | 26.8 | 87.2% | 0.7 | 99.7% |
| 2 | 25.9 | 87.7% | 0.6 | 99.7% |
| 3 | 25.8 | 87.7% | 3 | 98.6% |
| 4 | 25.8 | 87.7% | 0.7 | 99.7% |
| 5 | 26.5 | 87.4% | 4.8 | 97.7% |
| 6 | 26.9 | 87.2% | 0.9 | 99.6% |
| 7 | 26.3 | 87.5% | 5.1 | 97.6% |
| 8 | 28.3 | 86.5% | 2 | 99% |
| 9 | 25.9 | 87.7% | 1.6 | 99.2% |
| 10 | 26.7 | 87.3% | 1.8 | 99.1% |

The reaction virtually reached the equilibrium state after a reaction time of 4 h, over 10 cycles, with just under 90% conversion. After an overall reaction time of 22 h, with removal of water under reduced pressure, a conversion of >97% was achieved for all 10 batches. No significant loss of enzyme activity was observed across the 10 batches.

Example 2

Synthesis by a 3-Step Process in a 10 m$^3$ Reactor

The 10 m$^3$ reactor was equipped with a paddle stirrer, a heating jacket, a nitrogen sparger at the bottom of the reactor and a jet vacuum system. In addition, meshes were installed in the bottom outlet to retain the catalyst. Enzyme immobilization and reaction were carried out in the same reactor.

140 kg of Accurel MP 1000 and 1500 kg of ethanol were charged in the reactor and stirred for 0.5 h, after which the ethanol was drained off through the bottom outlet. 3000 kg of water were added to the reactor and 150 kg of Lipozyme CalB L added with stirring. The immobilization was carried out for 16 h at 25° C. The aqueous solution was drained off from the reactor and the retained immobilizate was washed once with water.

To the total immobilized enzyme in the reactor were added 6550 kg of a mixture of octanol and fatty acid (industrial mixture of octanoic acid and decanoic acid). The mixture was stirred for 4 h at 45° C. and atmospheric pressure. Stirring was stopped after 4 h and a sample was removed for determination of the acid number. After 30 min the water phase (approx. 350 kg) was drained off from the reactor and the reaction was restarted. The temperature was raised to 60° C., a jet vacuum of approx. 30 mbar was applied and the reaction mixture was purged with nitrogen. The batch was incubated for a further 12 h with stirring. After this reaction period the batch was drained off via the filtration mesh and finely filtered through a bag filter. In total, 9 batches were processed with the same enzyme without detecting any significant enzyme deactivation.

After a reaction number of 4 h, all batches had an acid number of 25-30, corresponding to a conversion of >85%. Following termination of the reaction, all batches had an acid number of <2, corresponding to a conversion of at least 99%, based on the fatty acid. The reaction product was clear and virtually colorless. In total, over 52 000 kg of product were prepared with a yield of over 98%.

Example 3

Product Quality of the Esters Prepared by the Process According to the Invention The product from example 2 was further purified by distillation and deodorized. To this end, the product was fed through a production distillation consisting of three columns connected in series. The product was metered in at a flow rate of 2000 kg/h and, in the first column, an initial fraction consisting of unconverted reactants was taken off at a rate of 90 kg/h. In the 2nd column, the ester was distilled overhead to improve color and, in the 3rd column, the ester was deodorized at 120° C. with 10% steam to improve odor.

The product thus obtained (mixture of octyl octanoate and octyl decanoate) had a saponification number of 210, an acid number of <0.1, an hydroxyl number of <0.1 and a peroxide number of <0.1. The Hazen color number was 10 and the cloud point was −12° C. The ester content by GC analysis was 99.4% (FIG. 1). In this FIGURE, the two major peaks are identifiable as octyl octanoate (~6 min RT) and octyl decanoate (~7 min RT).

Example 4

Enzyme Stability as a Function of Temperature

Lewatit VPOC 1600 (Lanxess) and commerically available lipase B ex *Candida antarctica* (Lipozyme CalB L from Novozymes) in a 1:1 ratio were stirred overnight at room temperature in 20 times the amount of water. The immobilized enzyme was filtered off and used directly for the synthesis.

In sealable bottles, 50 g of an equimolar mixture of octanol and fatty acid (industrial mixture of octanoic acid and decanoic acid) in each case were reacted with 2% by weight of immobilized enzyme (1 g). The mixtures were shaken for 22 h at 30° C., 45° C. and at 60° C. in parallel. Following this reaction period, the batch was filtered off and the conversion determined by measuring the acid number. In total, 9 batches were processed with the same enzyme at the 3 temperatures. The starting acid number of the fatty alcohol/fatty acid mixture was 210.

| Batch | Acid no. 30° C. | Conversion 30° C. | Acid no. 45° C. | Conversion 45° C. | Acid no. 60° C. | Conversion 60° C. |
|---|---|---|---|---|---|---|
| 1 | 30.9 | 85.3% | 32.8 | 84.4% | 35.3 | 83.2% |
| 2 | 26 | 87.6% | 40.8 | 80.6% | 34.7 | 83.5% |
| 3 | 24.3 | 88.4% | 32.6 | 84.5% | 36.2 | 82.8% |
| 4 | 26.4 | 87.4% | 29.4 | 86% | 36.4 | 82.7% |
| 5 | 26.8 | 87.2% | 29.7 | 85.9% | 91.3 | 56.5% |
| 6 | 31.2 | 85.1% | 31.2 | 85.1% | 155.2 | 26.1% |

-continued

| Batch | Acid no. 30° C. | Conversion 30° C. | Acid no. 45° C. | Conversion 45° C. | Acid no. 60° C. | Conversion 60° C. |
|---|---|---|---|---|---|---|
| 7 | 25.9 | 87.7% | 30.5 | 85.5% | 151.8 | 27.7% |
| 8 | 26.9 | 87.2% | 29.7 | 85.9% | 147.6 | 29.7% |
| 9 | 30.8 | 85.3% | 29.2 | 86.1% | 173.5 | 17.4% |

After a reaction time of 22 h at 30° C. and 45° C., no significant loss of enzyme activity is observed across the 9 batches. At 60° C., a significant loss of activity is observed from batch 5, while after 9 batches less than 25% of the starting conversion is achieved.

Example 5

Enzyme Stability as a Function of Temperature

Accurel MP 1000 (Membrana) was incubated for 1 h in a 10-fold excess of ethanol and then filtered off. The ethanol-moist Accurel MP 1000 and commercially available Lipase B ex *Candida antarctica* (Lipozyme CalB L from Novozymes) in a 1:1 ratio were stirred overnight at room temperature in 20 times the amount of water. The immobilized enzyme was filtered off and used directly for the synthesis.

In sealable bottles, 50 g of an equimolar mixture of octanol and fatty acid (industrial mixture of octanoic acid and decanoic acid) in each case were reacted with 2% by weight of immobilized enzyme (1 g). The mixtures were shaken for 22 h at 30° C., 45° C. and at 60° C. in parallel. Following this reaction period, the batch was filtered off and the conversion determined by measuring the acid number. In total, 9 batches were processed with the same enzyme at the 3 temperatures. The starting acid number of the fatty alcohol/fatty acid mixture was 210.

| Batch | Acid no. 30° C. | Conversion 30° C. | Acid no. 45° C. | Conversion 45° C. | Acid no. 60° C. | Conversion 60° C. |
|---|---|---|---|---|---|---|
| 1 | 27.2 | 87% | 33 | 84.3% | 36.3 | 82.7% |
| 2 | 25.8 | 87.8% | 30.7 | 85.4% | 38.2 | 81.8% |
| 3 | 28.1 | 86.6% | 32 | 84.8% | 35 | 83.3% |
| 4 | 33 | 84.3% | 30.6 | 85.4% | 34.2 | 83.7% |
| 5 | 25 | 88.1% | 30.6 | 85.4% | 47.5 | 77.4% |
| 6 | 24.4 | 88.4% | 30.8 | 85.3% | 95.6 | 54.5% |
| 7 | 26.3 | 87.5% | 30 | 85.7% | 135.9 | 35.3% |
| 8 | 26.3 | 87.5% | 30.3 | 85.6% | 143.6 | 31.6% |
| 9 | 26.7 | 87.3% | 30.2 | 85.6% | 149.4 | 28.9% |

After a reaction time of 22 h at 30° C. and 45° C., no significant loss of enzyme activity is observed across the 9 batches. At 60° C., a slight loss of activity from batch 5 and a significant loss from batch 6 is observed. After 9 batches less than 35% of the starting conversion is achieved.

A further batch was processed at 60° C. and at a reduced pressure of 20 mbar in a jacketed reactor. 800 g of the reactant mixture described above and 2% Lipase B ex *Candida antarctica* immobilized on Accurel MP 1000 were used per batch. In total, 8 batches were processed with continuous stirring and nitrogen sparging. Samples were taken after both 3 h and 22 h. No accumulation of water was observed.

| Batch | Acid no. 3 h | Conversion 3 h | Acid no. 22 h | Conversion 22 h |
|---|---|---|---|---|
| 1 | 8.9 | 95.8% | 3.1 | 98.5% |
| 2 | 8.5 | 95.9% | 5.1 | 97.6% |
| 3 | 9.9 | 95.3% | 0.4 | 99.8% |
| 4 | 25.0 | 88.1% | 0.4 | 99.8% |
| 5 | 16.6 | 92.1% | 0.6 | 99.7% |
| 6 | 91.9 | 56.2% | 5.2 | 97.5% |
| 7 | 169.6 | 19.2% | 40.5 | 80.7% |
| 8 | 170.2 | 19% | 66.3 | 68.4% |

At a reaction temperature of 60° C., also under conditions of reduced pressure and with continuous removal of water, a rapid deactivation of the catalyst occurs. After 4 cycles, even the sample taken at 3 h shows slowing of the reaction rate, while after 6-7 cycles full conversion is no longer achieved even after 22 h.

Examples 1, 4 and 5 were conducted with comparable amounts of enzyme and with the same mixture of reactants. In the 3-step procedure of the ester synthesis (example 1) with a reaction to reach equilbrium at 45° C. and a further conversion under reduced pressure at 60° C., no significant reduction of the enzyme activity is seen over 10 reaction cycles. In contrast, the direct reaction at 60° C. led, with both the Lewatit VPOC 1600 support (example 4) and Accurel MP 1000 (example 5), even after 5 cycles, to a significant reduction of the enzyme activity.

The comparison shows that particularly the reactants used in the examples exert a deactivating influence on the enzyme. Octanol has a strong solvent character and octanoic acid and decanoic acid are quite strong acids. At the same time, the deactivation of the enzyme is strongly dependent on the reaction temperature selected.

The three-step synthesis, in which >80% of the reactants are converted at a lower temperature in the first step and then the remaining 10-20% of the reactants at a higher temperature, leads to a significantly improved enzyme stability in comparison to the direct conversion of the reactants at high temperature. The three-step procedure is particularly suitable for the industrial implementation, since the removal of water under reduced pressure in the second reaction step works significantly better than at a lower temperature.

In further storage tests it was confirmed that the enzyme has a better stability in the ester produced than in the reactant mixture. The storage of the immobilizate for 1 month at 45° C. in the product mixture led to no significant reduction of the enzyme activity.

Comparative Example 1

Ester Synthesis Under Reduced Pressure in a 10 m³ Reactor

The immobilization and reaction was carried out in the same reactor as described in example 2. The immobilization was likewise carried out as described in example 2 and the reactant mixture and the ratio of biocatalyst and reactants were identical.

In the reactor, 6550 kg of a mixture of octanol and fatty acid (industrial mixture of octanoic acid and decanoic acid) were added to the total immobilized enzyme. The mixture was stirred for 4 h at 45° C. and sparged with nitrogen using a jet vacuum of 30 mbar. A sample was taken after 4 h and the amount of water present was analyzed. The acid number of the sample was 26, corresponding to a conversion of >87%.

It was found that water accumulates after 4 h in the reactor: approx. 75% of the amount of water formed could not be removed from the reactor by the vacuum pumps at a temperature of 45° C. To remove the water formed initially by evaporation at the stated temperature, approx. 16 h would have been required. Not until after complete removal of the water phases would the system have been able to react further.

It has been shown that, in typical production reactors for cosmetic and industrial esters having a size of 20-100 m³, the removal of water takes longer due to the relatively high fill level and unfavorable surface to volume ratio. Only by raising the reaction temperature to 80-100° C., for example, can the water be removed more rapidly. Since, however, the deactivation of the enzyme is very severe in this case, this process variant is not a suitable solution.

As was shown in inventive example 2, the reaction is stopped after 4 h so that the water phase can be removed from the reactor within a short time. Even at a lower temperature (30-45° C.), the reaction to reach equilibrium is achieved within about 4 h. After the water has been separated off, the reaction temperature can be raised to 60° C., for example, for better removal of the water phase without significant enzyme deactivation, since the major part of the reactants have already reacted. The whole reaction can thus be carried out within 12-20 h.

The invention claimed is:

1. A process for preparing esters from fatty alcohols and fatty acids comprising the steps:
   reaction of fatty alcohols of the formula $R^1$—OH, where $R^1$ is an aliphatic linear or branched hydrocarbon group having 6 to 22 carbon atoms, and fatty acids of the formula $R^2$—COOH, where $R^2$ is an aliphatic linear or branched hydrocarbon group having 6 to 22 carbon atoms, in the presence of a lipase at a temperature in the range of 30 to 50° C. without water removal, until the reaction equilibrium is achieved;
   removal of the water formed during the reaction after the reaction equilibrium is achieved; and
   completion of the reaction under reduced pressure at a temperature in the range of 50 to 80° C.
   wherein the lipase is used in an immobilized form.

2. The process according to claim 1, wherein the completion of the reaction is carried out in a stripping gas atmosphere.

3. The process according to claim 2, wherein the stripping gas comprises nitrogen, air, carbon dioxide, or argon.

4. The process according to claim 1, wherein a pressure of 100 to 10 000 Pa is applied during the completion of the reaction.

5. The process according to claim 4, wherein a pressure of 1500 to 4500 Pa is applied during the completion of the reaction.

6. The process according to claim 1, wherein the reaction is carried out at a temperature in the range of 35 to 45° C.

7. The process according to claim 1, wherein the completion of the reaction is carried out at a temperature in the range of 55 to 65° C.

8. The process according to claim 1, wherein the immobilized lipase is used in an amount of 0.5 to 5.0% by weight.

9. The process according to claim 1, wherein the fatty alcohols used are those whose linear or branched alkyl or alkenyl group has 8 to 18 carbon atoms.

10. The process according to claim 1, wherein the fatty acids used are those whose linear or branched alkyl or alkenyl group has 8 to 18 carbon atoms.

11. The process according to claim 1, wherein the ester preparation is carried out in a one-pot process.

12. The process according to claim 1 further comprising steps of purification and preservation.

13. The process according to claim 12, wherein a forerun distillation, a product distillation for improving color, a deodorization for optimizing odor, and/or an addition of antioxidants are carried out.

14. The process according to claim 1, wherein the reaction to equilibrium step is conducted in the absence of reduced pressure.

15. The process according to claim 1, wherein the reaction to equilibrium step is conducted with mechanical agitation.

16. The process according to claim 1, wherein the removal of the water step is conducted by decanting without mechanical agitation.

17. The process according to claim 1, wherein the lipase is *Candida antarctica* lipase B.

* * * * *